(12) United States Patent
Jeong et al.

(10) Patent No.: US 9,488,561 B2
(45) Date of Patent: Nov. 8, 2016

(54) TEST APPARATUS FOR EARLY LANDSLIDE DETECTION FULLY-CONNECTED WITH PORE WATER PRESSURE, SURFACE DISPLACEMENT AND SHEAR SURFACE

(71) Applicant: Korea Institute of Geoscience and Mineral Resource, Daejeon (KR)

(72) Inventors: Sueng Won Jeong, Busan (KR); Choon Oh Lee, DaeJeon (KR); Kyeong-Su Kim, Daejeon (KR); Byung-Gon Chae, Daejeon (KR); Young-Suk Song, Daejeon (KR); Junghae Choi, Daejeon (KR)

(73) Assignee: Korea Institute of Geoscience and Mineral Resources, Daejeon (KR)

( * ) Notice: Subject to any disclaimer, the term of this patent is extended or adjusted under 35 U.S.C. 154(b) by 177 days.

(21) Appl. No.: 14/537,623

(22) Filed: Nov. 10, 2014

(65) Prior Publication Data
US 2016/0047724 A1    Feb. 18, 2016

(30) Foreign Application Priority Data
Aug. 18, 2014 (KR) .............. 2014-0107051

(51) Int. Cl.
| G09B 23/40 | (2006.01) |
| G01N 3/24 | (2006.01) |
| G09B 23/12 | (2006.01) |
| G09B 23/10 | (2006.01) |
| G09B 23/08 | (2006.01) |

(52) U.S. Cl.
CPC ............. *G01N 3/24* (2013.01); *G09B 23/12* (2013.01); *G09B 23/08* (2013.01); *G09B 23/10* (2013.01); *G09B 23/40* (2013.01)

(58) Field of Classification Search
CPC ...... G09B 23/08; G09B 23/10; G09B 23/12; G09B 25/00; G06F 17/5009
USPC ................ 73/865.6, 863; 434/299
See application file for complete search history.

(56) References Cited

U.S. PATENT DOCUMENTS

| 9,068,309 | B2 * | 6/2015 | Jeong | ............... E02B 1/02 |
| 9,070,304 | B2 * | 6/2015 | Jeong | ............ G09B 23/12 |
| 2013/0255406 | A1 * | 10/2013 | Jeong | ............ G09B 23/12 |
| | | | | 73/865.6 |
| 2013/0263681 | A1 * | 10/2013 | Jeong | ............ G09B 23/12 |
| | | | | 73/865.6 |
| 2014/0227036 | A1 * | 8/2014 | Jeong | ............ G09B 23/40 |
| | | | | 405/79 |

FOREIGN PATENT DOCUMENTS

KR    10-2012-0073406 A    7/2012

* cited by examiner

*Primary Examiner* — Lisa Caputo
*Assistant Examiner* — Jonathan Dunlap
(74) *Attorney, Agent, or Firm* — Adam Warwick Bell; Matthew Rupart Kaser

(57) ABSTRACT

Disclosed herein is a test apparatus for early landslide detection fully-connected with pore water pressure, surface displacement and shear surface. The test apparatus calculates a factor of safety of a slope based on variation in pore water pressure, surface displacement and shear surface of a soil mass, and predicts a change in factor of safety, thus making early landslide detection possible. In the test apparatus, while a container of a slider is moved with a soil mass loaded into the container, shear surface and surface displacement environment is provided, and the shear strength and the shear stress of the soil mass can be calculated based on the pore water pressure and the weight of the soil mass. Thereby, the factor of safety of the soil mass can be calculated, and early landslide detection can be realized by using variation of the factor of safety of the slope.

14 Claims, 6 Drawing Sheets

TEST APPARATUS FOR EARLY LANDSLIDE DETECTION FULLY-CONNECTED WITH PORE WATER PRESSURE, SURFACE DISPLACEMENT AND SHEAR SURFACE

BACKGROUND OF THE INVENTION

1. Field of the Invention

The present invention relates generally to test apparatuses for early landslide detection and, more particularly, to a test apparatus for early landslide detection fully-connected with pore water pressure, surface displacement and shear surface, which calculates a factor of safety of a slope based on variation in pore water pressure, surface displacement and shear surface of a soil mass constituting landslide materials and predicts a change in factor of safety depending on small deformation of the ground, thus making early landslide detection possible.

2. Description of the Related Art

Generally, landslides refer to a collapse of slopes and are caused by various reasons, for example, torrential rainfall, earthquakes, snow melting, etc. In areas where there are many mountains because of geomorphological characteristics, areas where mountains or hills are cut for constructing roads or the like, or areas where landslide risk evaluation is necessary due to construction of dams, banks or the like, determining the stability of slopes is required. Furthermore, in areas where landslide occurrence frequency is relatively high, early detection of movement indicating a landslide is imminent and setting up disaster prevention measures are required. Landslides mainly occur because of earthquakes or localized heavy rain in summer. Such a landslide is a phenomenon in which in a slope having a slip plane (a failure plane) a soil mass above the slip plane is deformed. When the sum of shear forces on the slip plane is greater than the sum of resistance forces, a landslide is caused. When the slope collapses, the failure slope leads to a debris flow having different magnitudes depending on rainfall conditions and geomorphological conditions, and may result in property damage and/or loss of life.

To evaluate the stability of a slope, the factor of safety of the slope must be determined. The factor of safety is the ratio of shear strength to shear stress that is present at time of failure, that is, at a time when shear strength to shear stress reaches an equilibrium limit. In other words, the factor of safety is expressed as shear strength/shear stress. Typically, if the factor of safety is less than 1, the slope is analyzed as being unstable. However, although the factor of safety of the slope is suitable for determining whether the slope is stable or not, it is not easy to predict a failure time of the slope because the resultant force of the shear strength on the failure plane of the slope continuously varies. Thus, a test apparatus for early landslide detection, which can determine shear strength taking displacement of the ground surface where a slope is deformed and a pore water pressure of a failure plane into account and the degree of particle breakage on a shear surface, is required.

Meanwhile, a conventional technique pertaining to the present invention was proposed in Korean Patent Unexamined Publication No. 10-2012-0073406, entitled "Landslide calibration chamber test apparatus using artificial rainfall simulator." The apparatus according to this conventional technique includes a chamber which creates a slope, an artificial rainfall simulator which sprays artificial rain water onto the slope of the chamber, and an instrument device which measures the behavior of the slope.

In this conventional apparatus, debris flow materials are arranged in the longitudinal direction of the chamber, thus forming a slope. While the artificial rainfall simulator sprays artificial rain water, the behavior of the slope is measured.

However, the conventional apparatus varies only a supply rate of water using the artificial rainfall simulator but cannot provide the shear surface environment of the debris flow materials nor simulate surface displacement. Therefore, the conventional apparatus cannot calculate variation in factor of safety depending on the surface displacement and soil mass deformation.

PRIOR ART DOCUMENT

Patent Document (Patent document 0001) Korean Patent Unexamined Publication No. 10-2012-0073406

SUMMARY OF THE INVENTION

All references and publications mentioned in this disclosure are hereby incorporated by reference for all purposes.

Accordingly, the present invention has been made keeping in mind the above problems occurring in the prior art, and an object of the present invention is to provide a test apparatus for early landslide detection fully-connected with pore water pressure, surface displacement and shear surface, which simulates surface displacement resulting from a slope failure, calculates shear strength on the failure plane of the slope based on variation of pore water pressure depending on the surface displacement, and determines a factor of safety of the slope based on the calculated value, thus realizing early landslide detection based on variation in the factor of safety of the slope.

Another object of the present invention is to provide a test apparatus for early landslide detection fully-connected with pore water pressure, surface displacement and shear surface, which provides a shear surface formed on a shear surface in a shear band form and simulates a rough surface of a collapsed slope so that more reliable testing environments can be created.

In order to accomplish the above object, the present invention provides a test apparatus for early landslide detection fully-connected with pore water pressure, surface displacement and shear surface, the test apparatus including: a frame; a flume installed on the frame so as to be adjustable in angle, the flume providing a slope for landslide materials; a slider coupled to the flume so as to be movable in a longitudinal direction of the flume, with a soil mass loaded into the slider, the soil mass constituting the landslide materials, the slider providing a shear surface of the soil mass, wherein the slider moves along with the soil mass in the longitudinal direction of the flume and simulates a surface displacement of an upper part of the soil mass and a slope failure of a lower surface of the soil mass; and a calculation unit calculating shear strength and shear stress on a failure plane of the slope based on pore water pressure and weight of the soil mass depending on the movement of the slider, and calculating a factor of safety of the slope based on the calculated shear strength and shear stress.

The calculation unit may comprise: a weight sensor installed in a bottom plate of the slider, the weight sensor measuring the weight of the soil mass depending on the movement of the slider; a pore water pressure sensor installed in an inner surface of the slider, the pore water pressure sensor measuring the pore water pressure in the soil mass; and a calculation server calculating the shear strength and shear stress of the slope based on measured values transmitted from the weight sensor and the pore water pressure sensor and then calculating the safety factor of the slope based on the calculated shear strength and shear stress.

The calculation server may use: a following [formula 1] to calculate the shear strength on the failure plane of the slope; a following [formula 2] to calculate the shear stress on the failure plane of the slope; and a following [formula 3] to calculate the safety factor of the slope.

shear strength=cohesion+effective stress×tan (internal friction angle)

effective stress=total stress−pore water pressure of pore water pressure sensor  [formula 1]

(the cohesion, the internal friction angle and the total stress are preset constants)

shear stress=the sum of forces causing activities obtained by the weight measured by the weight sensor  [formula 2]

factor of safety=shear strength/shear stress  [formula 3]

The calculation unit may further include: a sensor holder formed in the inner surface of the slider, the sensor holder having a depression shape, with the pore water pressure sensor embedded in the sensor holder; and a sensor filter provided in an upper end of the sensor holder, the sensor filter allowing water to enter the sensor holder and filtering out foreign materials other than water.

The slider may include: a container movably provided on the flume, the container having a box shape open on an upper end thereof, with the soil mass loaded in the container so that the container simulates the shear surface on the lower surface of the soil mass; a cover covering the open upper end of the container; and an actuator movably supporting the container and controlling movement of the container or a speed of the movement thereof.

The actuator may include a hydraulic cylinder connected to an end of the container to support the container, the hydraulic cylinder contracting or extending a length thereof and thus moving the container.

The slider may further include a collapsed-slope simulation unit providing a rough surface to a bottom surface of the container and thus simulating a rough surface of a collapsed slope on the lower surface of the soil mass.

The collapsed-slope simulation unit may include: a winding roller provided on a first side plate of the container; a rough surface member wound around the winding roller and interposed between the bottom surface of the container and the lower surface of the soil mass while a front end of the rough surface member is pulled towards a second side plate of the container, the rough surface member being made of a material having a predetermined surface roughness to provide a rough surface; a pulling-out roller provided at a position spaced apart from the container, the pulling-out roller winding the front end of the rough surface member therearound and pulling the rough surface member from the winding roller; and a slot formed in the second side plate of the container so that the rough surface member is linearly connected to the pulling-out roller through the slot.

The rough surface member may be made of any one of a non-woven fabric having a predetermined surface roughness, a sand paper and a member having protrusions on a surface thereof to provide a predetermined surface roughness.

The collapsed-slope simulation unit may further include a water sealing member provided in the slot, the water sealing member coming into close contact with the rough surface member and prevent water contained in the soil mass from leaking out of the container through the slot.

The slider may further include a plurality of flume rollers rotatably provided on and arranged along a bottom surface of the flume, the flume rollers providing a slip plane for the container.

The slider may further include a rainfall simulator unit installed in the cover, the rain simulation unit supplying water onto an upper portion of the soil mass and providing a simulated rain environment to the soil mass.

The rain simulation unit may include: a plurality of spray nozzles installed in and arranged along a lower surface of the cover, the spray nozzles spraying water towards the soil mass; and a supply pump supplying water to the spray nozzle.

The test apparatus may further include a camera provided above the flume, the camera photographing movement of the slider to determine a position of the slider or conditions of the soil mass loaded in the slider depending on the movement of the slider.

As described above, in a test apparatus for early landslide detection fully-connected with pore water pressure, surface displacement and shear surface according to the present invention, while a container of a slider is moved with a soil mass loaded into the container, a shear surface and surface displacement environment is provided, and the shear strength and the shear stress of the soil mass can be calculated based on the pore water pressure and the weight of the soil mass. Thereby, the factor of safety of the soil mass can be calculated based on the pore water pressure and the surface displacement, and early landslide detection can be realized by using variation of the factor of safety of the slope.

Furthermore, the movement of the container of the slider and the speed of movement thereof can be controlled by an actuator, whereby various types of surface displacement scenarios can be simulated.

Moreover, provided on the inner surface of the bottom plate of the container, a rough surface member can provide a rough surface to the lower surface of the soil mass while being unwound out of a winding roller. Thereby, taking geomorphological characteristics (of the bottom area) of a landslide zone into account, a rough surface can be simulated. Therefore, a more reliable test environment can be provided.

Because the rough surface member is linearly connected to a pulling-out roller through a slot, which is formed in a side plate of the container, the rough surface member can be smoothly pulled towards the pulling-out roller while providing a rough surface to the soil mass. Provided in the slot, a water sealing member can prevent water contained in the soil mass from leaking out of the container.

In addition, a pore water pressure sensor of a calculation unit is received in a sensor holder and covered with a sensor filter. Therefore, the pore water pressure sensor can be prevented from malfunctioning attributable to foreign materials.

If flume rollers are installed on the bottom of the flume, the container can be more smoothly moved.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Hereinafter, a preferred embodiment of the present invention will be described in detail with reference to the attached drawings. In the following description of the present invention, detailed explanation of well known functions or configurations will be omitted.

Figure 1:
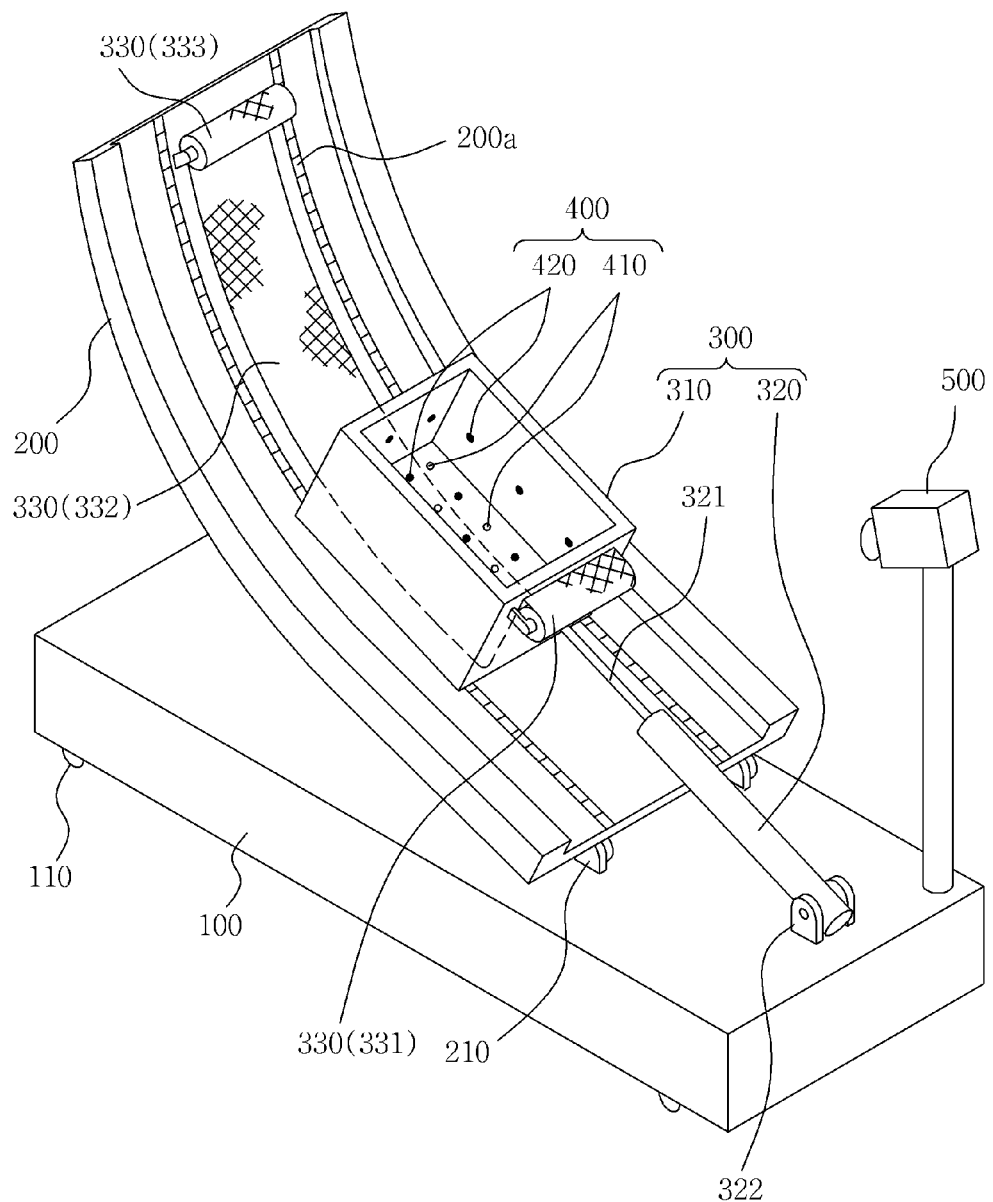
FIG. 1 is a perspective view illustrating a test apparatus for early landslide detection fully-connected with pore water pressure, surface displacement and shear surface according to the present invention.
Figure 2:
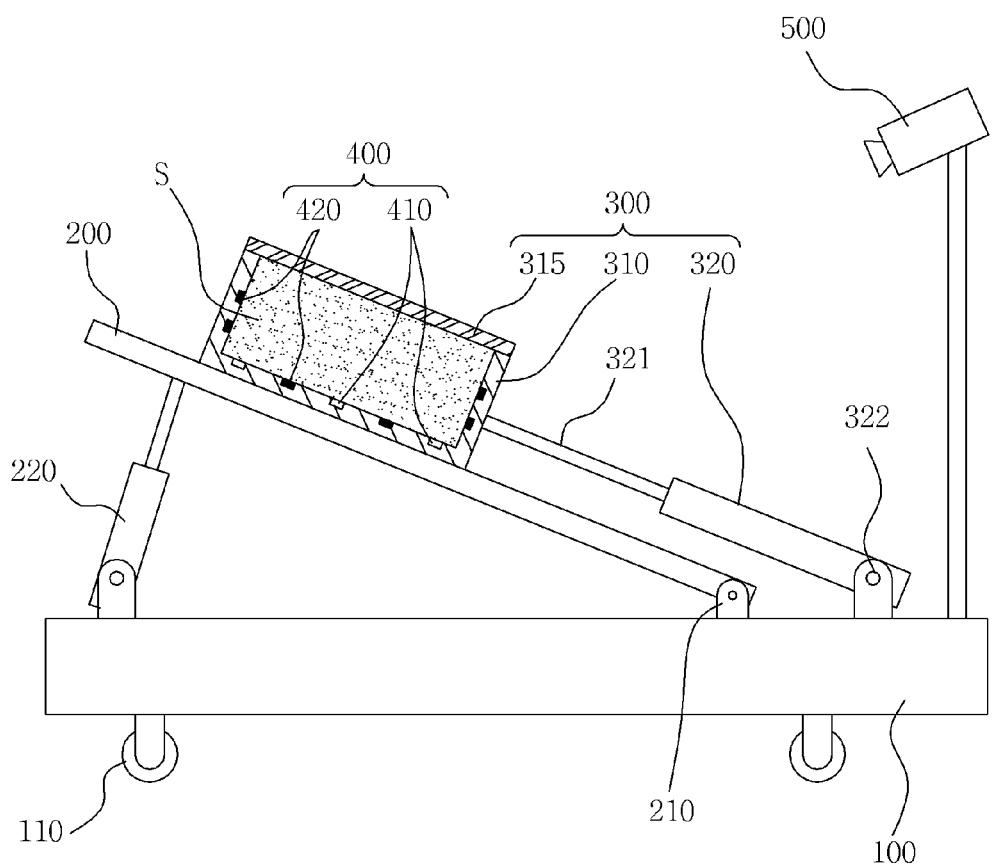
FIG. 2 is a longitudinal sectional view showing a test apparatus for early landslide detection according to the present invention.

As shown in FIGS. 1 and 2, a test apparatus for early landslide detection fully-connected with pore water pressure, surface displacement and shear surface according to the present invention includes a frame 100, a flume 200, a slider 300 and a calculation unit 400.

The frame 100 is an element that provides support force to install the test apparatus of the present invention indoors. The frame 100 is provided in a form corresponding to the shape and size of a test room.

For example, as shown in FIG. 1, the frame 100 may have a bogie shape with casters 110 provided under the bottom thereof and be thus configured so as to be movable. Unlike the structure shown in the drawing, the frame 100 may be configured in such a way that it is fixed indoors using a combination of a horizontal frame and a vertical frame.

The flume 200 forms an inclined surface of a slope for soil mass constituting landslide materials in a linear or non-linear curved form, thus providing a ramp for use in simulating slope behavior or surface displacement. The flume 200 is installed on the frame 100 so as to be adjustable in angle such that the flume 200 can provide a variety of test environments.

For instance, as shown in FIG. 2, the angle of inclination of the flume 200 may be adjusted in such a way that a first end of the flume 200 is rotatably coupled to the frame 100 by a hinge 210, and a second end of the flume 200 is moved upwards or downwards by a lift unit such as the hydraulic cylinder 220.

Alternatively, the angle of inclination of the flume 200 may be adjusted in such a way that the second end of the flume 200 is connected to a hoist (not shown) and is pulled upwards by the hoist.

Unlike the embodiment shown in the drawings, depending on conditions of a test, the flume 200 may comprise a plurality of flumes connected to each other.

As shown in FIG. 1, the flume 200 may be designed such that it is curved in a semicircular shape to make it possible to simulate a circular failure phenomenon.

Figure 4:
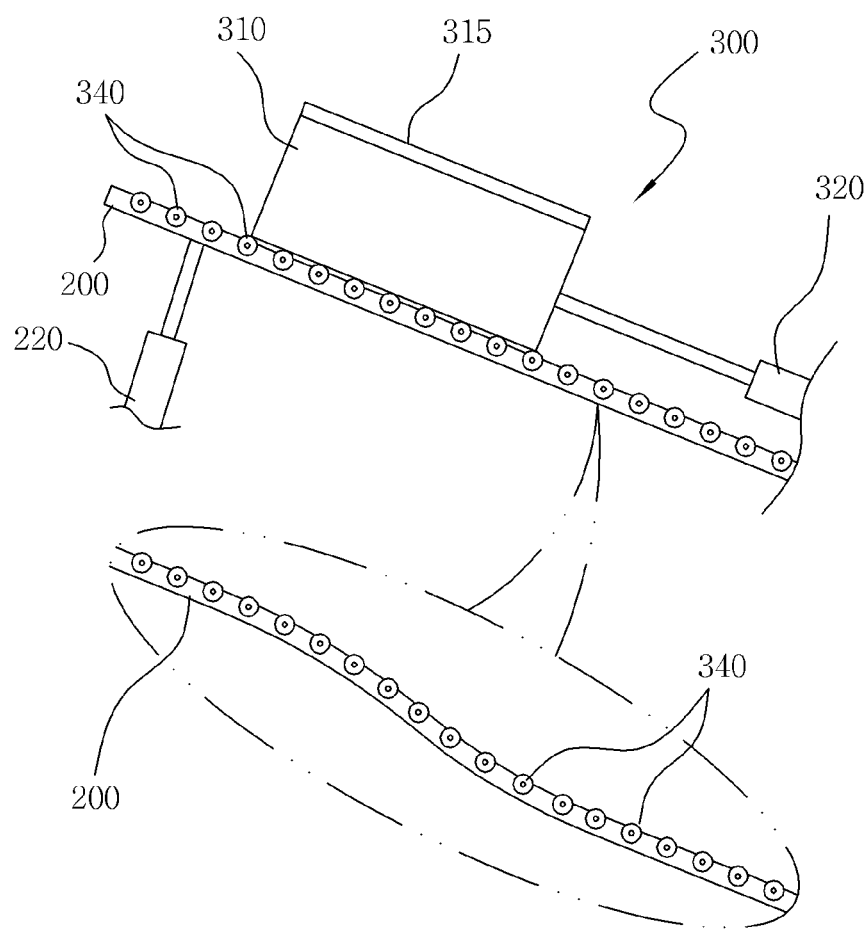
FIG. 4 is a view showing the construction of another embodiment of a flume illustrated in FIG. 2.

Alternatively, as shown in FIG. 2, the flume 200 may be configured to have a linear structure. As a further alternatively, the flume 200 may be manufactured in a curved shape, as shown in FIG. 4.

Here, the words "soil mass" means a soil sample, which refers to landslide materials of a landslide occurrence site that reflect compaction conditions and permeability characteristics of soil and which is loaded into a container that will be explained later herein. The soil sample loaded into the container 310 is hardened by ramming under a predetermined pressure so as to simulate the density of the landslide occurrence site and is charged into the container 310 to the height of the container 310 or to a predetermined height.

The slider 300 is an element that simulates the shear surface of the soil mass S constituting landslide materials and moves along with the soil mass S so as to simulate surface displacement or slope failure.

For example, as shown in FIGS. 1 and 2, the slider 300 includes the container 310, a cover 315 and an actuator 320.

As shown in FIG. 1, movably provided on the flume 200, the container 310 has a box shape open on an upper end thereof. As shown in FIG. 2, soil mass S is loaded into the container 310 without leakage. The container 310 simulates a shear surface on the lower surface of the soil mass S loaded therein.

Figure 3:
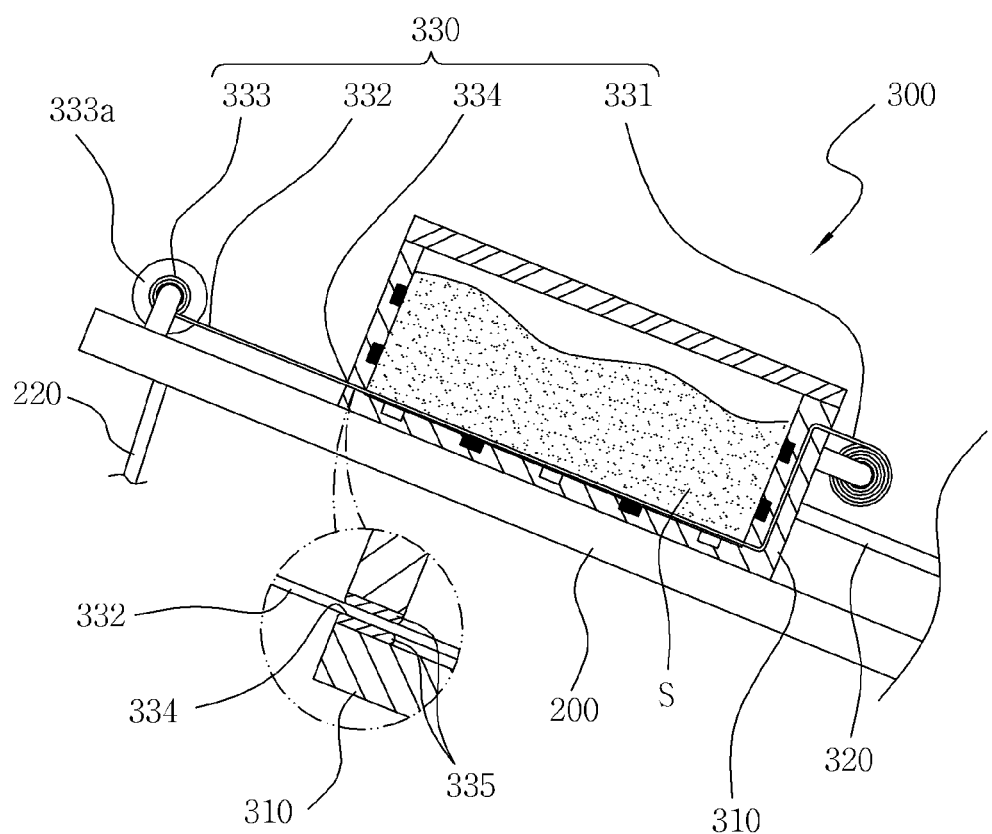
FIG. 3 is a longitudinal sectional view showing another embodiment of a slider illustrated in FIG. 2.

Depending on conditions of a test, as shown in FIG. 2, the container 310 may be fully filled with soil mass S or, alternatively, as shown in FIG. 3, it may be partially filled with soil mass S.

As shown in FIG. 2, a weight sensor 410 and a pore water pressure sensor 420 of the calculation unit 400, which will be explained in detail later herein, are installed at predetermined positions in the inner surface of the container 310.

As shown in FIG. 1, it is preferable that the container 310 be placed on rails 200a so as to be movable along the rails 200a.

In an embodiment, the rails 200a protrude from the upper surface of the flume 200, extend in the longitudinal direction of the flume 200, and are configured to guide the opposite sides of the container 310. That is, the rails 200a can guide movement of the container 310 in such a way that protrusions, which are the rails 200a and grooves, are respectively formed in the surfaces of the flume 200 and container 310 facing each other.

As shown in FIGS. 2 and 3, the cover 315 covers the open upper end of the container 310 to prevent the soil mass S or water from leaking out of the container 310.

Preferably, covering the container 310, the cover 315 is made of transparent material to make it possible to observe the interior of the container 310. The reason for this is to allow a camera 500 to capture an image of the interior of the container 310.

The actuator 320 supports the container 310 and moves it. In addition, the actuator 320 controls the movement and speed of the container 310 and thus simulates a slope failure attributable to surface displacement or movement of the soil mass S.

As shown in FIGS. 1 and 2, the actuator 320 includes a hydraulic cylinder provided with a rod 321 which is connected to an end of the container 310 and supports the container 310. Using hydraulic pressure, the actuator 320 extends or retracts the rod 321, thus moving the container 310.

As shown in FIG. 1, the hydraulic cylinder of the actuator 320 is coupled to the frame 100 by a hinge 322 so that when the angle of inclination of the flume 200 is adjusted, the hydraulic cylinder can rotate around the hinge 322 while supporting the container 310.

Meanwhile, as shown in FIG. 3, the slider 300 according to the present invention may further include a collapsed-slope simulation unit 330.

The collapsed-slope simulation unit 330 provides frictional force to the inner surface of the container 310 and simulates a rough surface of a collapsed slope on the lower surface of the soil mass (the soil sample).

For example, as shown in FIG. 3, the collapsed-slope simulation unit 330 includes a winding roller 331, a rough surface member 332, a pulling-out roller 333 and a slot 334.

The winding roller 331 is rotatably installed on a lower side surface of the container 310, as shown in FIGS. 1 and 3.

The pulling-out roller 333 is rotatably installed on the flume 200 at a position spaced apart from the container 310, as shown in FIGS. 1 and 3.

The pulling-out roller 333 is installed to be in an idling state. As shown in FIG. 1, the pulling-out roller 333 may be a stationary type which cannot be automatically rotated. Alternatively, as shown in FIG. 3, the pulling-out roller 333 may be configured such that it is automatically rotated by the drive force of a drive motor 333a. This will be explained in detail later herein.

Referring to FIG. 3, the rough surface member 332 is interposed between the inner surface of the bottom plate of the container 310 and the lower surface of the soil mass S and provides a rough surface to the lower surface of the soil mass S.

The rough surface member 332 is made of material having a high roughness. As shown in FIG. 3, the rough surface member 332 is wound around the winding roller 331, and a front end of the rough surface member 332 extends along the bottom plate of the container 310 and is coupled to the pulling-out roller 333. As the container 310 moves, the rough surface member 332 is unwound from the winding roller 331 so as to provide a rough surface to the lower surface of the soil mass S, thus simulating a rough surface of a collapsed slope.

For example, the rough surface member 332 may be made of a non-woven fabric having a high surface roughness, sand paper or a member having uneven protrusions on the surface thereof to provide a predetermined surface roughness.

Preferably, as shown in FIG. 3, the rough surface member 332 is configured such that it is inserted into a side plate of the container 310 and extracted along the bottom plate of the container 310. In this way, the rough surface member 332 comes into contact with only the lower surface of the soil mass S without making contact with a side surface of the soil mass S.

As shown in FIG. 1, if the pulling-out roller 333 is a stationary type roller, it functions merely to hold the front end of the rough surface member 332 so that the rough surface member 332 can be unwound from the winding roller 331 when the container 310 moves.

In detail, as the container 310 is moved downwards by the actuator 320 and the winding roller 331 is moved downwards along with the winding roller 331, the rough surface member 332 is unwound from the winding roller 331 by the supporting force of the pulling-out roller 333, thus shearing the lower surface of the soil mass S.

That is, when the pulling-out roller 333 is a stationary type, a shear rate of the soil mass S resulting from the rough surface member 332 is proportional to the speed of movement of the container 310. This case can simulate conditions in which although a slope seems to be largely deformed, a shear part in the slope is not largely deformed.

Unlike this, as shown in FIG. 3, if the pulling-out roller 333 is a rotary type roller, the speed of revolution thereof can be controlled by the drive motor 333a. Therefore, the rough surface member 332 can be pulled out of the winding roller 331 at a lower or higher speed than the speed of movement of the container 310.

Furthermore, even when the container 310 is in a stationary state, the pulling-out roller 333 may rotate using the drive force of the drive motor 333a and pull the rough surface member 332 out of the winding roller 331, thus simulating a shear surface on the lower surface of the soil mass S.

Therefore, when the pulling-out roller 333 is a rotary type roller, it is possible to simulate conditions in which although a slope of a mountain area seems to have moved only slightly significant deformation on a shear part has occurred.

The slot 334 has a length corresponding to the width of the rough surface member 332 and is formed in a corresponding side plate of the container 310 so that the rough surface member 332 is linearly connected to the pulling-out roller 333 through the slot 334.

Therefore, the rough surface member 332 can be more smoothly pulled by the rotation of the pulling-out roller 333, whereby frictional force can be reliably provided to the lower surface of the soil mass S.

As shown in the enlarged view of FIG. 3, a water sealing member 335 is preferably provided in the slot 334.

For example, the water sealing member 335 may be made of a rubber packing. As shown in the enlarged view, the water sealing member 335 comes into close contact with the rough surface member 332, thus preventing water contained in the soil mass S from leaking out of the container 310 through the slot 334.

Referring to FIG. 3, in the same manner, the slot 334 may also be formed in the side plate of the container 310 on which winding roller 331 is installed.

As shown in FIG. 4, the slider 300 may further include a flume roller 340.

The flume roller 340 is an element which provides a slip plane for the container 310. As shown in FIG. 4, the flume roller 340 comprises a plurality of flume rollers which are rotatably installed on the flume 200 and arranged in the longitudinal direction of the flume 200.

As shown in FIG. 4, even when the flume 200 has a curved form, the flume rollers 340 may also be arranged along the curved surface of the flume 200.

Figure 7:
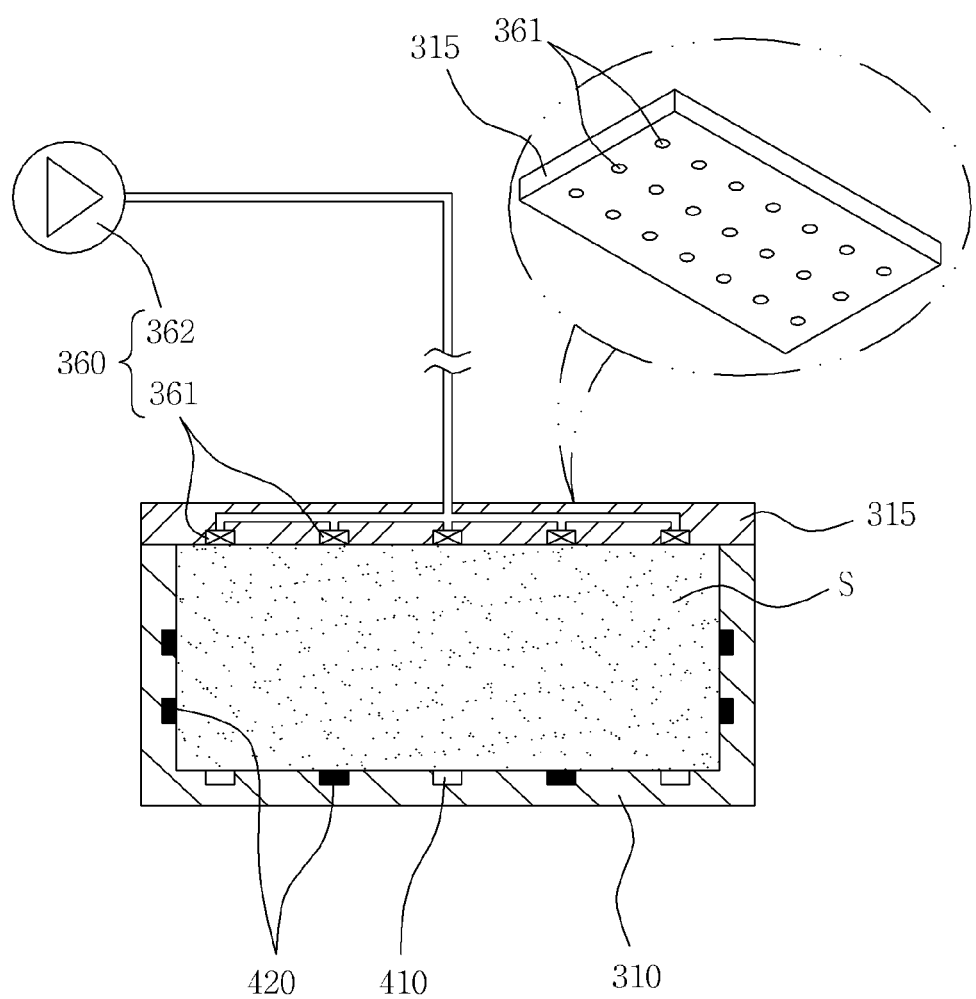
FIG. 7 is a longitudinal sectional view showing a further embodiment of the slider illustrated in FIG. 2.

As shown in FIG. 7, the slider 300 may further include a rain simulation unit 360.

The rain simulation unit 360 is an element which sprays water onto the upper part of the soil mass S and thus provides a simulated rain environment to the soil mass S.

For example, as shown in FIG. 7, the rain simulation unit 360 includes a spray nozzle 361 and a supply pump 362.

The spray nozzle 361 comprises a plurality of spray nozzles which are installed and arranged in a lower surface of the cover 315 to spray water from the supply pump 362 onto the soil mass S.

The supply pump 362 supplies water to the spray nozzles 361, and a water supply rate may be constant or variable depending on conditions of a test.

In other words, the rain simulation unit 360 provides test environment that can maintain the degree of saturation of the ground constant or vary it when ground deformation is caused.

As shown in FIG. 1, the camera 500 may be provided above the flume 200.

Disposed above the flume 200, the camera 500 photographs the movement of the container 310 to measure displacement of the soil mass S with respect to a predetermined point above the container 310 according to the movement of the container 310. Preferably, the camera 500 comprises a high-resolution digital camera, a precision terrestrial LiDAR (Light Detection And Ranging) or the like to precisely measure the position of the soil mass S over time.

Furthermore, it is preferable that the camera 500 be connected to the actuator 320 so that the camera 500 can photograph the container 310 while interlocking with the operation of the actuator 320.

In other words, the orientation of a head of the camera 500 varies depending on variation of the length of the hydraulic cylinder of the actuator 320. In this way, the camera 500 photographs the container 310 while varying the photographing angle.

The calculation unit 400 measures the weight of the soil mass S and pore water pressures of the bottom and side surfaces of the soil mass S resulting from movement of the container 310 of the slider 300, calculates the shear strength and shear stress of the slope based on the measured results, and calculates a safety factor of the slope based on the calculated shear strength and shear stress.

Figure 5:
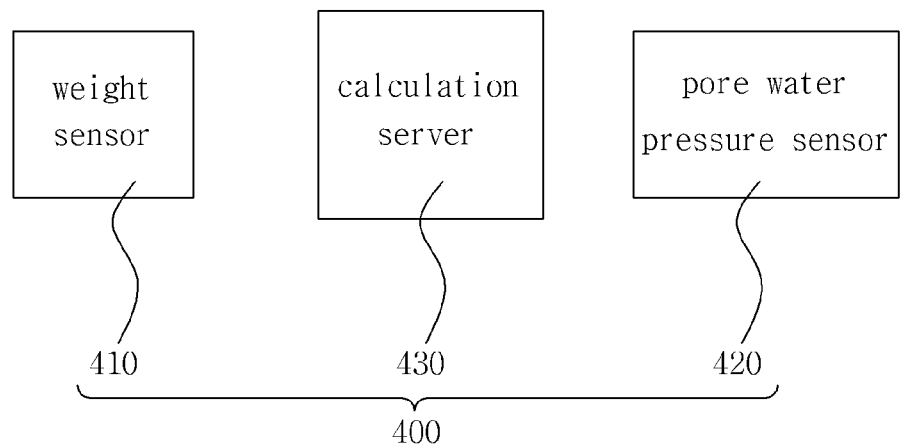
FIG. 5 is a block diagram showing a calculation unit according to the present invention.

For example, as shown in FIGS. 2 and 5, the calculation unit 400 includes the weight sensor 410, the pore water pressure sensor 420 and a calculation server 430.

As shown in FIG. 2, installed in the bottom plate of the container 310, the weight sensor 410 measures the weight of the soil mass S and transmits it to the calculation server 430, which will be explained in detail later herein.

Preferably, the weight sensor 410 comprises a plurality of weight sensors installed and arranged in the bottom plate of the container 310, as shown in FIG. 2. The weight sensors provide not only the gross weight of the soil mass S but also weight distribution of the soil mass S by the movement of the container 310 to the calculation server 430.

The pore water pressure sensor 420 measures a pore water pressure of water flowing through the soil mass S. As shown in FIG. 1, the pore water pressure sensor 420 comprises a plurality of pore water pressure sensors installed in the bottom plate and the side plates of the container 310.

As shown in FIG. 2, the pore water pressure sensors 420 along with the weight sensors 410 may be fixed in place or, alternatively, they may be movably configured and arranged in the soil mass S at different positions.

The pore water pressure sensors 420 measure pore water pressures of the portions at which they are installed, and transmit measured values to the calculation server 430, thus providing the varying pore water pressures depending on the surface displacement resulting from the movement of the container 310.

Figure 6:
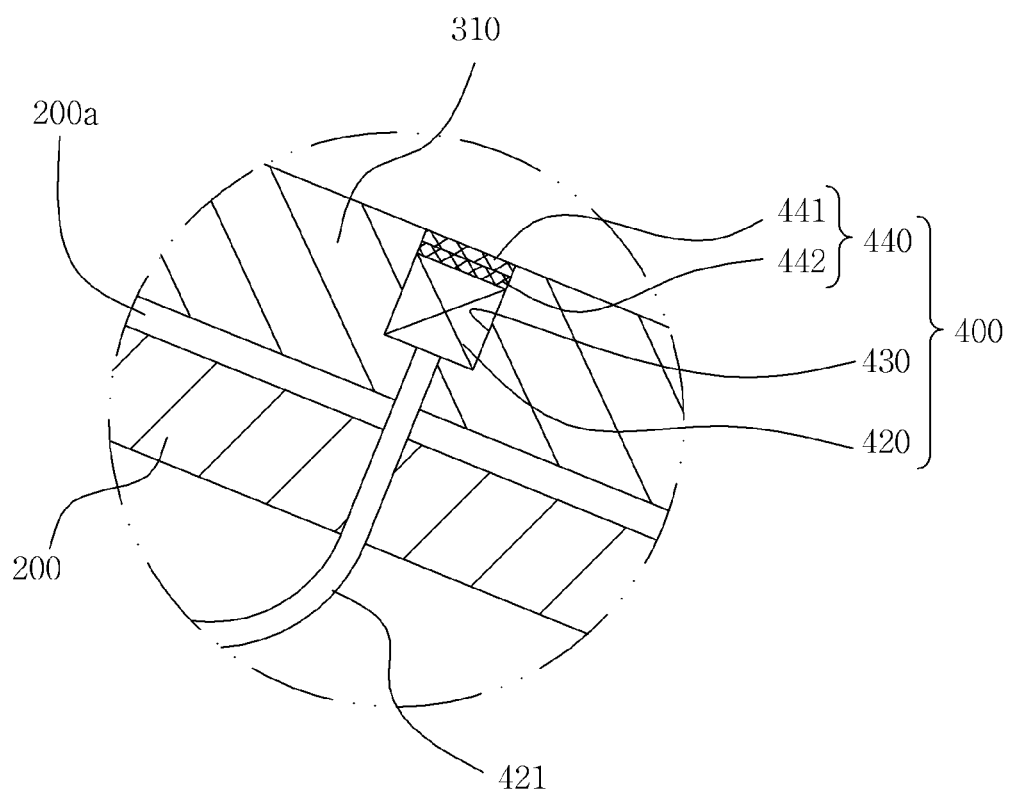
FIG. 6 is an enlarged view showing a pore water pressure sensor illustrated in FIG. 2.

As shown in the enlarged view of FIG. 6, each pore water pressure sensor 420 is received in a sensor holder 430 and is covered with a sensor filter 440.

The sensor holder 430 has a depression shape and is formed in the inner surface of the container 310. The pore water pressure sensor 420 is embedded in the corresponding sensor holder 430.

As shown in the enlarged view of FIG. 6, a cable 421 connected to the pore water pressure sensor 420 passes through the sensor holder 430 and the flume 200, extends a predetermined length, and is wound around a cable reel (not shown). As the container 310 moves, the cable 421 is unwound from the cable reel.

The sensor filter 440 functions to filter out foreign materials. As shown in the enlarged view of FIG. 6, the sensor filter 440 is installed in an upper portion of the sensor holder 430 and allows only water to enter the sensor holder 430 while filtering out foreign materials other than water.

Thereby, the pore water pressure sensor 420 can measure the pressure of only water that has passed through the sensor filter 440. Therefore, the pore water pressure sensor 420 can be prevented from malfunctioning.

For example, the sensor filter 440 includes a metal filter 441 and a paper filter 442.

Disposed in an outermost portion of the sensor holder 430, the metal filter 441 comes into direct contact with the soil mass S and primarily filters out foreign materials.

The paper filter 442 is disposed inside the metal filter 441 and secondarily filters out foreign materials other than water.

The calculation server 430 calculates the shear strength and the shear stress of the slope based on measured values transmitted from the weight sensors 410 and the pore water pressure sensors 420 and then calculates a safety factor.

The calculation server 430 includes a computer, which contains a control program and is connected to the weight sensors 410 and the pore water pressure sensors 420 by cables 421.

The calculation server 430 uses the following formula 1 to calculate the shear strength of a slope failure plane.

$$\text{shear strength} = \text{cohesion} + \text{effective stress} \times \tan(\text{internal friction angle})$$

$$\text{effective stress} = \text{total stress} - \text{pore water pressure of pore water pressure sensor} \quad [\text{Formula 1}]$$

Here, the cohesion and the internal friction angle are geotechnical constants of the soil mass S, and the total stress is a constant depending on the soil mass S.

That is, the shear strength is inversely proportional to the volume of the pore water pressure, which is a factor determining the effective stress.

Furthermore, the calculation server 430 uses the following formula 2 to calculate the shear stress of the soil mass S.

$$\text{shear stress} = \text{the sum of forces causing activities obtained by weights measured by the weight sensors} \quad [\text{Formula 2}]$$

That is, the shear strength of the soil mass S is force, with which the soil mass S flows downwards, and is proportional to the weight of the soil mass S.

The calculation server 430 uses the following formula 3 to calculate a factor of safety of the slope based on the calculated shear strength and shear stress.

$$\text{Factor of safety} = \text{shear strength}/\text{shear stress} \quad [\text{Formula 3}]$$

As the shear strength is reduced or the shear stress is increased, the factor of safety of the slope is reduced. When the factor of safety is 1 or less, a slope failure is caused.

In brief, the calculation server 430 calculates the shear strength and the shear stress of the lower surface of the soil mass S at each point, while the soil mass S is moved by the container 310, and then calculates the safety factor of the slope.

The test apparatus may be configured in such a way that while the container 310 continuously moves at a preset speed under the control of the actuator 320, the calculation server 430 continuously calculates the factor of safety of the slope. Alternatively, the test apparatus may be configured in such a way that while the container 310 moves by stages, the calculation server 430 calculates the factor of safety of the slope at each of preset points.

As a result, a test can predict a variation in factor of safety according to a pattern of movement of the slope or a time change. Based on this, occurrence of a landslide can be early detected using the pore water pressure, the shear surface and the surface displacement of a landslide danger zone.

As described above, in the test apparatus for early landslide detection fully-connected with pore water pressure, surface displacement and shear surface according to the present invention, while the container 310 of the slider 300 is moved with the soil mass S loaded into the container 310, the shear surface and the surface displacement are provided according to shear time, and the shear strength and the shear stress of the soil mass can be calculated based on the pore water pressure and the weight of the soil mass. Thereby, the factor of safety can be calculated based on the pore water pressure and the surface displacement, and early landslide detection can be realized by using a variation of the factor of safety of the slope.

Furthermore, the movement of the container of the slider 300 and the speed of movement thereof can be controlled by the actuator 320, whereby various types of surface displacement scenarios can be simulated.

Moreover, provided on the inner surface of the bottom plate of the container 310, the rough surface member 332 is moved by the operation of the pulling-out roller 333 so that frictional force can be provided to the lower surface of the soil mass S. Thereby, a rough surface of a collapsed slope can be simulated. Hence, a more reliable test environment can be created.

Because the rough surface member 332 is linearly connected to the pulling-out roller 333 through the slot 334, which is formed in a side plate of the container 310, the rough surface member 332 can be smoothly pulled towards the pulling-out roller 333 while providing a rough surface to the soil mass. Provided in the slot 334, the water sealing member 335 can prevent water contained in the soil mass S from leaking out of the container.

Furthermore, if the rain simulation unit 360 is provided in the slider 300, it can provide a test environment, which can maintain the degree of saturation of the ground constant or increase it when ground deformation is caused.

In addition, the pore water pressure sensor 420 of the calculation unit 400 is received in the sensor holder 430 and covered with the sensor filter 440. Therefore, the pore water pressure sensor 420 can be prevented from malfunctioning attributable to foreign materials.

If the flume rollers 340 are installed on the bottom of the flume 200, the container 310 can be more smoothly moved.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A test apparatus for early landslide detection fully-connected with pore water pressure, surface displacement and shear surface, the test apparatus comprising:
    a frame;
    a flume installed on the frame so as to be adjustable in angle, the flume providing a slope for landslide materials;
    a slider coupled to the flume so as to be movable in a longitudinal direction of the flume, with a soil mass loaded into the slider, the soil mass constituting the landslide materials, the slider providing a shear surface of the soil mass, wherein the slider moves along with the soil mass in the longitudinal direction of the flume and simulates a surface displacement of an upper part of the soil mass and a slope failure of a lower surface of the soil mass; and
    a calculation unit calculating shear strength and shear stress on a failure plane of the slope based on pore water pressure and weight of the soil mass depending on the movement of the slider, and calculating a factor of safety of the slope based on the calculated shear strength and shear stress.

2. The test apparatus as set forth in claim 1, wherein the calculation unit comprises:
    a weight sensor installed in a bottom plate of the slider, the weight sensor measuring the weight of the soil mass depending on the movement of the slider;
    a pore water pressure sensor installed in an inner surface of the slider, the pore water pressure sensor measuring the pore water pressure in the soil mass; and
    a calculation server calculating the shear strength and shear stress of the slope based on measured values transmitted from the weight sensor and the pore water pressure sensor and then calculating the factor of safety of the slope based on the calculated shear strength and shear stress.

3. The test apparatus as set forth in claim 2, wherein the calculation server uses:
    a following [formula 1] to calculate the shear strength on the failure plane of the slope;
    a following [formula 2] to calculate the shear stress on the failure plane of the slope; and
    a following [formula 3] to calculate the factor of safety of the slope shear strength=cohesion+effective stress×tan (internal friction angle)

effective stress=total stress−pore water pressure of pore water pressure sensor          [formula 1]

(the cohesion, the internal friction angle and the total stress are preset constants)

shear stress=the sum of forces causing activities obtained by the weight measured by the weight sensor          [formula 2]

factor of safety=shear strength/shear stress.          [formula 3]

4. The test apparatus as set forth in claim 2, wherein the calculation unit further comprises:
    a sensor holder formed in the inner surface of the slider, the sensor holder having a depression shape, with the pore water pressure sensor embedded in the sensor holder; and
    a sensor filter provided in an upper end of the sensor holder, the sensor filter allowing water to enter the sensor holder and filtering out foreign materials other than water.

5. The test apparatus as set forth in claim 1, wherein the slider comprises:
    a container movably provided on the flume, the container having a box shape open on an upper end thereof, with the soil mass loaded in the container so that the container simulates the shear surface on the lower surface of the soil mass;
    a cover covering the open upper end of the container; and
    an actuator movably supporting the container and controlling movement of the container or a speed of the movement thereof.

6. The test apparatus as set forth in claim 5, wherein the actuator comprises
a hydraulic cylinder connected to an end of the container to support the container, the hydraulic cylinder contracting or extending a length thereof and thus moving the container.

7. The test apparatus as set forth in claim 5, wherein the slider further comprises
a collapsed-slope simulation unit providing a rough surface to a bottom surface of the container and thus simulating a rough surface of a collapsed slope on the lower surface of the soil mass.

8. The test apparatus as set forth in claim 7, wherein the collapsed-slope simulation unit comprises:
a winding roller provided on a first side plate of the container;
a rough surface member wound around the winding roller and interposed between the bottom surface of the container and the lower surface of the soil mass while a front end of the rough surface member is pulled towards a second side plate of the container, the rough surface member being made of a material having a predetermined surface roughness to provide a rough surface;
a pulling-out roller provided at a position spaced apart from the container, the pulling-out roller winding the front end of the rough surface member therearound and pulling the rough surface member from the winding roller; and
a slot formed in the second side plate of the container so that the rough surface member is linearly connected to the pulling-out roller through the slot.

9. The test apparatus as set forth in claim 8, wherein the rough surface member is made of any one of a non-woven fabric having a predetermined surface roughness, a sand paper and a member having protrusions on a surface thereof to provide a predetermined surface roughness.

10. The test apparatus as set forth in claim 8, wherein the collapsed-slope simulation unit further comprises
a water sealing member provided in the slot, the water sealing member coming into close contact with the rough surface member and prevent water contained in the soil mass from leaking out of the container through the slot.

11. The test apparatus as set forth in claim 5, wherein the slider further comprises
a plurality of flume rollers rotatably provided on and arranged along a bottom surface of the flume, the flume rollers providing a slip plane for the container.

12. The test apparatus as set forth in claim 5, wherein the slider further comprises
a rain simulation unit installed in the cover, the rain simulation unit supplying water onto an upper portion of the soil mass and providing a simulated rain environment to the soil mass.

13. The test apparatus as set forth in claim 12, wherein the rain simulation unit comprises:
a plurality of spray nozzles installed in and arranged along a lower surface of the cover, the spray nozzles spraying water towards the soil mass; and
a supply pump supplying water to the spray nozzle.

14. The test apparatus as set forth in claim 1, further comprising
a camera provided above the flume, the camera photographing movement of the slider to determine a position of the slider or conditions of the soil mass loaded in the slider depending on the movement of the slider.

* * * * *